United States Patent [19]

Oishi et al.

[11] Patent Number: 5,108,178
[45] Date of Patent: Apr. 28, 1992

[54] ATOMIC ABSORPTION SPECTROPHOTOMETER AND ELECTROMAGNETIC SHUT-OFF VALVE FOR USE THEREIN

[75] Inventors: Konosuke Oishi, Mito; Katsuhito Harada, Katsuta; Masamichi Tsukada, Ibaraki; Kazuo Moriya; Toyoharu Okumoto, both of Katsuta, all of Japan

[73] Assignee: Hitachi, Ltd., Tokyo, Japan

[21] Appl. No.: 500,880

[22] Filed: Mar. 29, 1990

[30] Foreign Application Priority Data

Mar. 31, 1989 [JP] Japan .................................. 1-78256

[51] Int. Cl.$^5$ .......................... G01J 3/30; G01N 21/74
[52] U.S. Cl. .................................................... 356/312
[58] Field of Search ...................... 356/311–312, 356/244, 36, 315, 417; 137/375

[56] References Cited

U.S. PATENT DOCUMENTS

| | | | |
|---|---|---|---|
| 2,664,779 | 1/1954 | White | 356/417 |
| 3,788,752 | 1/1974 | Salvin et al. | 356/36 |
| 3,871,827 | 3/1975 | Seiler et al. | 356/36 |
| 3,958,595 | 5/1976 | Al et al. | 137/375 |
| 4,146,050 | 3/1979 | Graves | 137/375 |
| 4,221,482 | 9/1980 | Macourt | 356/36 |
| 4,660,976 | 4/1987 | Falk | 356/312 |

FOREIGN PATENT DOCUMENTS

| | | | |
|---|---|---|---|
| 58-41338 | 3/1983 | Japan | 356/312 |
| 2036359A | 6/1980 | United Kingdom | |

OTHER PUBLICATIONS

Lundgren et al., "A Temperature-Controlled Graphite Tube Furnace for the Determination of Trace Metals in Solid Biological Tissue", Talanta, vol. 21, pp. 257–264, Apr. 1974.

Colaneri, "Solenoid Valve Basics", Instruments and Contr. System, vol. 52, No. 8, 1979.

Primary Examiner—F. L. Evans
Assistant Examiner—K. P. Hantis
Attorney, Agent, or Firm—Antonelli, Terry, Stout & Kraus

[57] ABSTRACT

An atomic absorption spectrophotometer includes a sample-atomizing portion for ashing and atomizing a sample, a power source operable to supply electric current to the sample-atomizing portion, a controller for controlling the operation of the power source, a pair of pressure regulators for setting a flow rate of an inert gas according to an ashing step and an atomization step in the sample-atomizing portion, a pair of movable valves respectively provided downstream of and connected to the pair of pressure regulators, and a filter device provided between the pair of movable valves and the sample-atomizing portion. Either of the pair of movable valves is activated into open or closed condition in synchronism with the operation of the power source so as to select the flow rate of the inert gas into the sample-atomizing portion. An electromagnetic shut-off valve for use in the atomic absorption spectrophotometer includes a valve housing having a valve chamber, and a movable valve body housed in the valve chamber. The movable valve body is movable between open and closed positions so as to open and close a gas flow line. The wall of the valve chamber is coated with a non-metallic material.

21 Claims, 4 Drawing Sheets

ATOMIC ABSORPTION SPECTROPHOTOMETER AND ELECTROMAGNETIC SHUT-OFF VALVE FOR USE THEREIN

BACKGROUND OF THE INVENTION

This invention relates generally to an atomic absorption spectrophotometer and an electromagnetic shut-off valve for use therein, and more particularly to an atomic absorption spectrophotometer suited for measuring trace elements with a good reproducibility and an electromagnetic shut-off valve for use therein.

A sample-atomizing portion comprising a graphite tube furnace has been extensively used as means for atomizing a sample in an atomic absorption analysis. A conventional atomic absorption spectrophotometer of this type comprises a sample-atomizing portion for effecting the drying, ashing (incinerating) and atomization of a sample, a power source operable under the control of a controller so as to supply electric current to the sample-atomizing portion, a first pressure regulator for setting an input pressure of an inert gas (e.g. argon gas), a second pressure regulator for adjusting the flow rate of the inert gas, a movable valve, such as an electromagnetic shut-off valve, controlled by the controller so as to operate in synchronism with the operation of the power source, and a flow meter provided downstream of and communicated to the movable valve so as to measure and monitor the gas flow rate. The power source supplies electric current to the sample-atomizing portion under the control of the controller so as to heat the sample-atomizing portion to temperatures necessary for effecting the drying, ashing and atomization of the sample. This conventional atomic absorption spectrophotometer has a high sensitivity, since the sample is atomized in a highly dense condition in a graphite tube furnace, and the spectrophotometer can make a quantitative analysis of trace elements having a concentration on the order of ppb ($10^{-9}$) and having about a weight of about $10^{-11}$ g. Therefore, it is said that a close attention must be paid to the absorption analysis. More specifically, measurements obtained by the atomic absorption spectrophotometer are influenced or affected by the environment in which the spectrophotometer is placed, the contamination of a sample container, variations in sampling amount. Thus, such measurements may be subjected to variations. For example, it is known that when dust in the air, which includes alkaline metals, Si, Zn, Al, etc., is included into a sample, measured values different from an expected value are intermittently obtained to vary widely. If a sample container is even slightly contaminated, the reproducibility of measurements is not expected. Further, when taking a sample from a highly viscous material such as a human serum the amount of the sample is varied, thus making it difficult to achieve a satisfactory reproducibility, which results in variations in measurements. Because of the high sensitivity of a prior atomic absorption spectrophotometer employing a graphite tube furnace, it has been considered unavoidable to intermittently obtain such measurements greatly different from the expected values.

To deal with such variations of measurements, it has been a common practice to effect the measurement two or three times with respect to the same sample and to determine a reliable measured value within a certain range of the variations of two or three measurements.

SUMMARY OF THE INVENTION

The inventor of the present invention has found that variations in measurements obtained by a prior atomic absorption spectrophotometer are due not only to dust in the air, the contamination of a sample container and variations in sampling amount, but also to other causes. More specifically, in the measurement of Al and Cu in a human serum by an atomic absorption spectrophotometer, variations in measurements of Al are caused not only by dust and impurities entering into the atomic absorption spectrophotometer from the outside but also by aluminum powder (hereinafter referred to as "abrasion powder") resulting from an electromagnetic shut-off valve of a gas flow system of the spectrophotometer. The present invention is based on the above knowledge.

It is an object of this invention to provide an atomic absorption spectrophotometer which prevents entry of foreign matter into a sample-atomizing portion so as to prevent the generation of abnormal signals, thereby providing measurements with a good reproducibility.

Another object of the invention is to provide an electromagnetic shut-off valve which does not produce abrasion powder of worn metal which will be detrimental to the atomic absorption measurement.

According to the present invention, there is provided an atomic absorption spectrophotometer, in which an amount of an inert gas supplied to a sample-atomizing portion is changed by the operation of a movable valve according to an ashing step and an atomization step which are effected at the sample-atomizing portion, and which is provided with filter means between the movable valve and the sample-atomizing portion.

DESCRIPTION OF THE PREFERRED EMBODIMENT OF THE INVENTION

Figure 1:
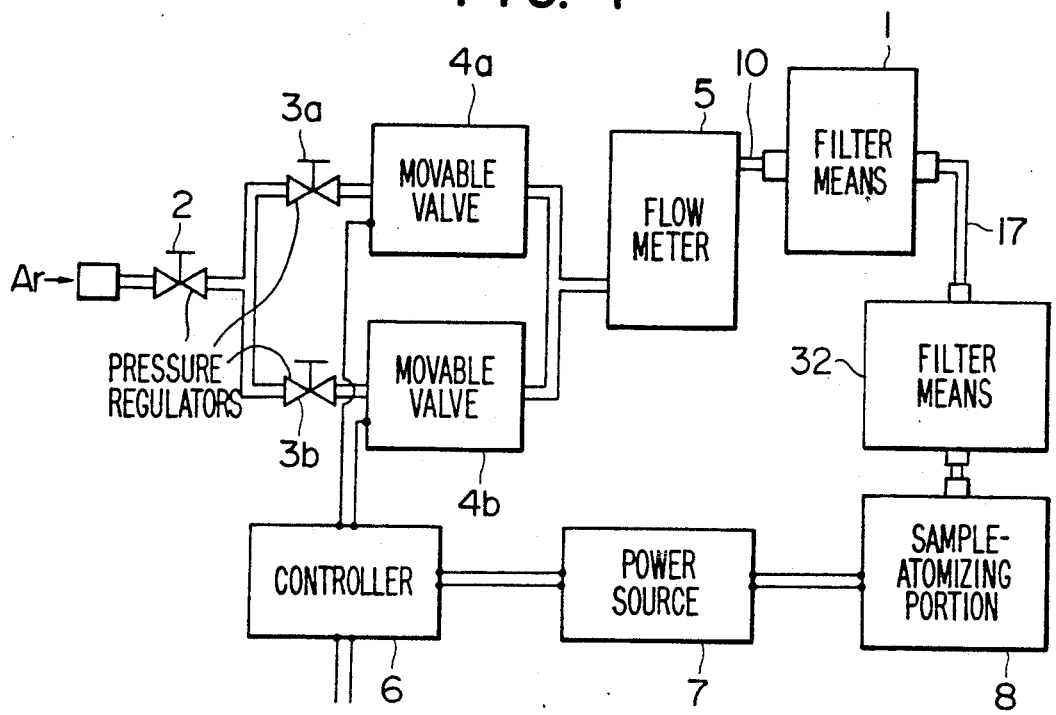
FIG. 1 is a schematic view of an atomic absorption spectrophotometer according to the present invention.

FIG. 1 shows an atomic absorption spectrophotometer according to the present invention. This spectrophotometer comprises a sample-atomizing portion 8 for effecting the drying, ashing (incinerating) and atomization of a sample, a power source 7 operable under the control of a controller 6 so as to supply electric current to the sample-atomizing portion 8, a first pressure regulator 2 for setting an input pressure of an inert gas such as argon gas, a pair of second pressure regulators 3a and 3b set for adjusting the flow rate of the inert gas, a pair of movable valves 4a and 4b operable in synchronism with the operation of the power source 7 under the control of the controller 6, a flow meter 5 of the float type provided downstream of and connected to the movable valves 4a and 4b for measuring and monitoring the gas flow rate, and a filter means 1 provided downstream of the flow meter 5 for removing foreign matter from argon gas. The power source 7 supplies electric current to the sample-atomizing portion 8 under the control of the controller 6 so as to heat the sample-atomizing portion 8 to temperatures required for effecting the drying, ashing and atomization of the sample. The inert gas (argon gas) is introduced into the sample-atomizing portion 8 to prevent the oxidation of a graphite tube furnace and also to discharge steam, organic decomposition products and incomplete-combustion substances (which are produced from the sample during the heating thereof) to the outside. The first pressure regulator 2 is set, for example, at 6 kg/cm². One second pressure regulator 3a is so set that the flow rate of argon gas is 5 ml/min. when one movable valve 4a is open and the other movable valve 4b is closed. The other second pressure regulator 3b is so set that the flow rate of argon gas is 200 ml/min. when the one movable valve 4a is closed and the other movable valve 4b is open. Each of the movable valves 4a and 4b is, for example, in the form of an electromagnetic shut-off valve, and comprises a movable valve body and a valve housing having a valve body receiving chamber. The opening and closing of the movable valves 4a and 4b are controlled by the controller 6 in synchronism with the various heating steps of the sample-atomizing portion 8. The filter means 1 removes, from argon gas, dust in the air, contaminants in a sample container, abrasion powder resulting from the movable valves 4a and 4b, and so on. The filter means 1 is provided immediately downstream of the flow meter 5. If another filter means 32 is provided immediately upstream of the sample-atomizing portion 8, foreign matter can be removed from argon gas more effectively. However, as indicated, such a filter means 32 is optional.

Figure 2:
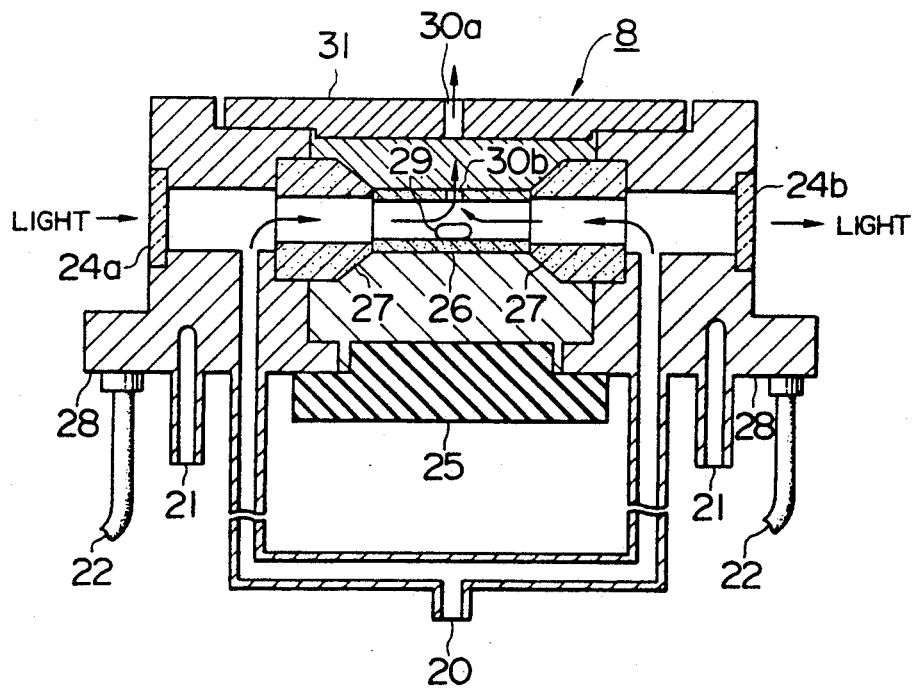
FIG. 2 is a vertical cross-sectional view of a graphite tube furnace of the spectrophotometer.

FIG. 2 shows the sample-atomizing portion 8 in detail. In the sample-atomizing portion 8, a graphite tube 26 is used as a heating member of a high density, and has an inner diameter of 5 mm, an outer diameter of 7 mm, a length of 30 mm and a resistivity of 13±2 mmΩ. A sample (solution) 29 collected in a microsyringe or the like is introduced into the graphite tube 26 through sample introduction holes 30a and 30b. A mounting body 28 is made of a metal of a good electrical conductivity, and has a cooling water hole 21. Cooling water is caused to flow through the cooling water hole 21 to keep the mounting body 28 at a constant temperature so as to prevent thermal deformation of an insulating plate 25 and an openable lid 31. Electric current is supplied from the power source 7 to the graphite tube 26 via electric wires 22, the mounting body 28 and graphite terminals 27, thereby heating the graphite tube 26. Usually, the graphite tube 26 is heated to a temperature of 3,000° C. A ray of light for the atomic absorption measurement passes through a window 24a, the interior (internal bore) of the graphite tube 26 and a window 24b, the two windows 24a and 24b being made of quartz. Argon gas, after passing through the filter means 1, flows into the interior of the graphite tube 26 through an argon gas inlet 20 of the sample-atomizing portion 8, and discharges therefrom unnecessary gases, such as steam, thermal decomposition gases of organic substances and steam of atoms of inorganic substances, to the outside.

Figure 3:
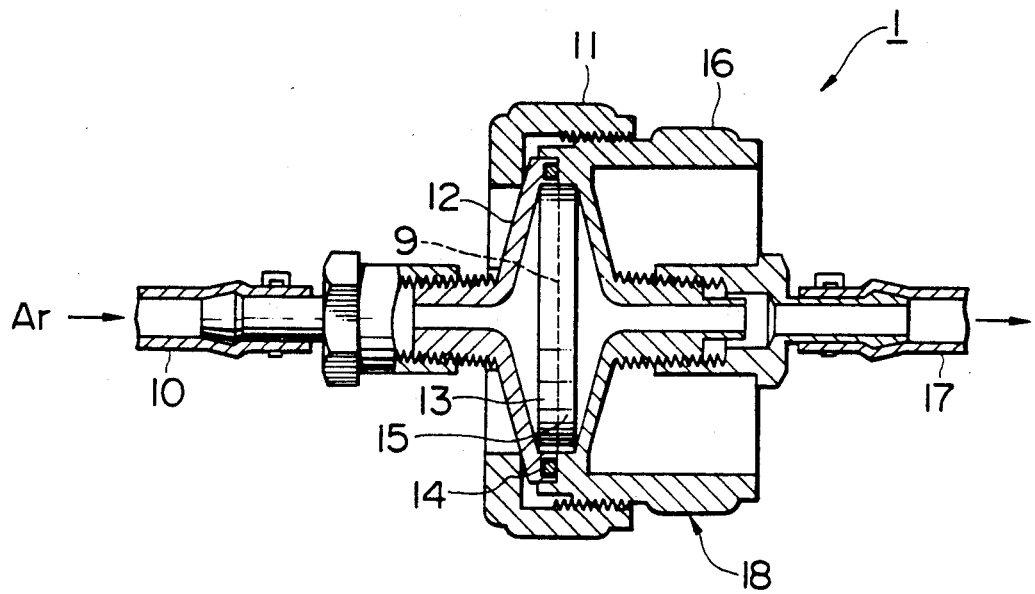
FIG. 3 is a vertical cross-sectional view of a filter holder of the spectrophotometer.
Figure 4:
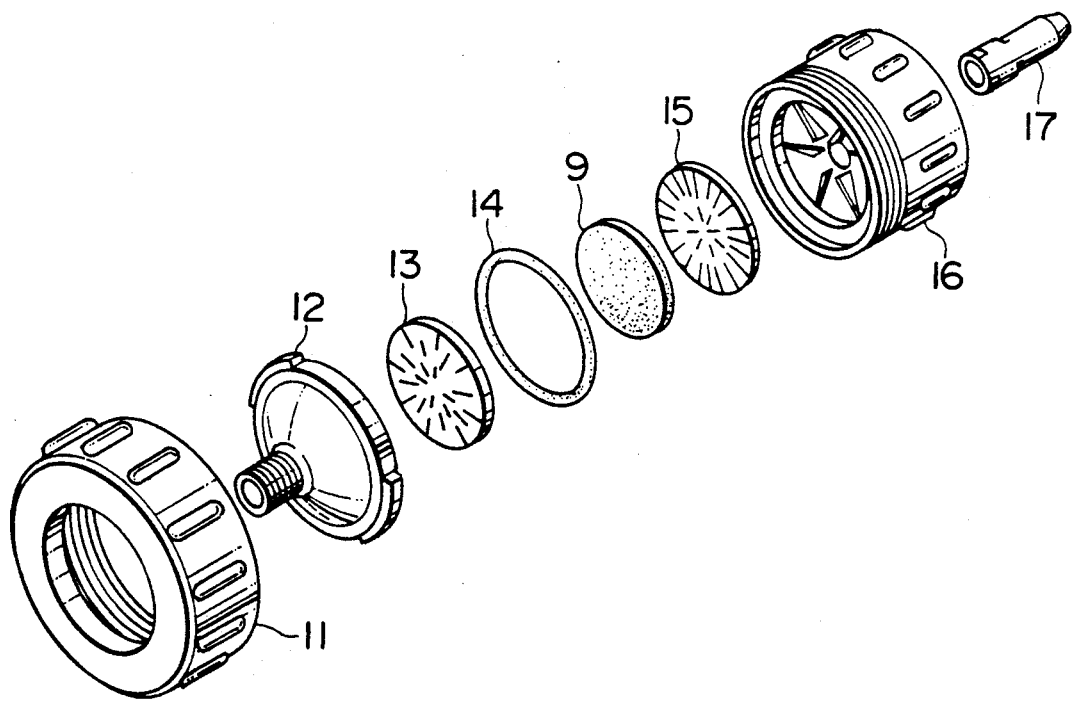
FIG. 4 is an exploded perspective view of the filter holder.

FIGS. 3 and 4 show the filter means 1 in detail. This filter means 1 comprises a filter element 9 and a filter holder 18 for holding the filter element 9. Here in this embodiment, the filter element 9 comprises a perforated disc of polytetrafluoroethylene having a diameter of 47 mm and a thickness of 0.05 to 0.1 mm, the diameter of the perforations (perforation diameter) being 0.05 to 3 μm. Preferably, the filter element 9 has a large area so as to reduce a resistance to the flow of the gas, and also is preferably made of a polymeric organic film. Alternatively, the filter element may be made of any other suitable material such as nitrocellulose and the like which will not produce fine powder affecting the atomic absorption analysis. The filter holder 18 includes an outer case 11 connected to an inlet pipe 10, an inner case 16 connected to an outlet pipe 17, a pair of holder plates 13 and 15 for holding the filter element 9 therebetween, and a clamp element 12. The outer case 11 is internally threaded, and the inner case 16 is externally threaded, so that the two cases 11 and 16 are threadedly connected together in a releasable manner. With this arrangement, the filter element 9 which becomes blind or clogged after a long period of use can be easily replaced by a new one. Upon threaded connection of the outer case 11 to the inner case 16, the clamp element 12 presses an O-ring 14 and the holder plates 13 and 15 against the inner case 16, thereby holding these members 14, 13 and 15 against movement. In a prior atomic absorption spectrophotometer which is not provided with the filter means of the present invention, the percentage of occurrence of abnormal measurements is 3 to 5%. On the other hand, in the atomic absorption spectrophotometer of the present invention, the percentage of occurrence of abnormal measurements is reduced to 2 to 3% where the filter element has a perforation diameter of 3 μm, and also such percentage is reduced to 0.1 to 0.3% where the filter element has a perforation diameter of 0.05 to 0.5 μm. Thus, in the atomic absorption spectrophotometer of the present invention, the occurrence of abnormal measurements is practically at an almost negligible level.

An atomic absorption measurement was carried out using the atomic absorption spectrophotometer of the present invention and a prior atomic absorption spectrophotometer not provided with the filter means. The measurement was conducted on the conditions (heating temperature and heating time of the graphite tube and the flow rate of argon gas) mentioned in Table 1 below.

TABLE 1

| Step | Heating conditions | | Argon gas | |
|---|---|---|---|---|
| | Temperature (°C.) | Time (sec) | Flow rate (ml/min) | Time (sec) |
| Drying | 80 to 90 | 60 | 200 | 60 |
| Ashing | 600 to 900 | 20 | 200 | 15 |
| | | | 5 | 5 |
| Atomization | 2900 | 5 | 5 | 5 |
| Cleaning | 3200 | 5 | 200 | 5 |
| Cooling | Room temperature | 60 until room temperature | 0 | |

Usually, the drying temperature is 80° to 90° C., and the drying time is 60 sec. The ashing temperature is determined according to a sample being analyzed and the kinds of elements being analyzed. For example, in the analysis of Al in a human serum the ashing temperature is 600° to 900° C., and the ashing time is 20 sec. The atomization temperature is 2,900° C., and the atomization time is 5 sec. The cleaning is effected by evaporating the residual ash in the graphite tube, and the cleaning temperature corresponds to the maximum temperature (for example, 3,200° C.) of the graphite tube. The cleaning time is 5 sec. The cooling is effected to the room temperature, and the time required for the cooling is 60 sec. The flow rate of argon gas is controlled in synchronism with each heating step, and this flow rate is zero at the final step (the cooling step) since argon gas is not required for this cooling step. The rate of flow of argon gas into the graphite tube furnace is controlled for the following reasons:

(a) Since argon gas is expensive, argon gas is caused to flow only when necessary, and the supply of this gas is stopped when unnecessary, thereby saving the running cost.

(b) It is necessary to flow a relatively large amount (200 ml/min) of argon gas so as to rapidly discharge steam and smoke (which results from incomplete combustion), produced from the sample solution during the drying and ashing steps, to the outside so that such steam and smoke will not contaminate the interior of the graphite tube.

(c) In the atomization step, the light ray for the measurement, when passing through a layer of steam of the element being analyzed, is absorbed in a resonance absorption phenomenon, and this absorption becomes greater as the atomic steam density becomes higher. Therefore, in order to detect a trace amount of atoms, the atomic steam is required to reside in the graphite tube as long as long as possible. For this reason, it is necessary either to stop the supply of argon gas or to reduce the amount of supply to such a level (several ml/min) which will not lower the measurement sensitivity. Also, since it is necessary to keep the flow rate of argon gas constant in the atomization step, it is necessary to change the flow rate immediately before the atomization step.

Figure 5:
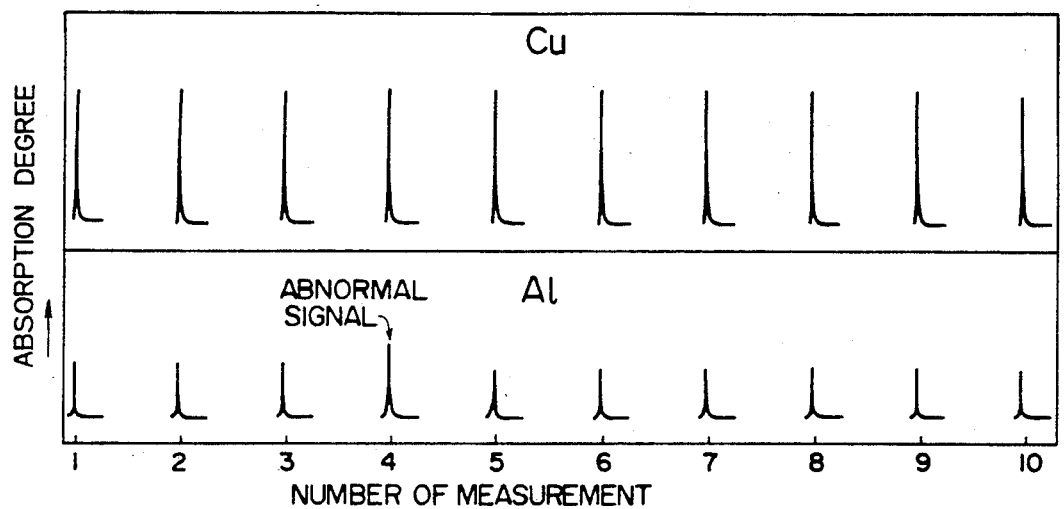
FIG. 5 is a diagrammatical illustration showing atomic absorption spectra of Al and Cu in a human serum man, obtained using a human prior art atomic absorption spectrophotometer.

FIG. 5 shows the results obtained when simultaneously analyzing Al and Cu in a human serum under the conditions shown in Table 1, using a prior atomic absorption spectrophotometer not provided with the above filter means. The ordinate represents absorption degree, and the abscissa represents the number of the measurement. The amount of a sample was 0.02 ml, and the number of measurements was 10. As is clear from FIG. 5, only with respect to Al, an extraordinarily high absorption degree was measured at the fourth measurement, but no abnormal measurement was recognized with respect to Cu. This indicates that the cause for such abnormal measurement is not due to variations in the amount of the sample. In FIG. 5, the abnormal signal of Al at the fourth measurement has two peaks, and the first peak is a main peak, and the subsequent peak is an abnormal peak. It is assumed that the reason why such an abnormal peak is developed is that Al entering the graphite tube furnace was heated at a low-temperature portion spaced from the center of the graphite tube furnace to cause a time lag in the atomization. From this, it is understood that an extraordinarily large amount of Al was not contained in the sample. The abnormal signal (the percentage of occurrence: 3 to 5%) with respect to Al is produced due to the fact that foreign matter containing Al is introduced into the graphite tube furnace for some reason, and there is a high possibility that such foreign matter is borne and transferred by the argon gas into the graphite tube furnace. Therefore, the electromagnetic shut-off valve, which was provided in the gas flow system and was well considered to produce such foreign matter, was disassembled, and its interior was inspected. The electromagnetic shut-off valve in question comprises a movable body made of iron with a plastic coating for opening and closing the valve and a cylinder made of Al material for housing the movable body. Since the movable body has the plastic coating, it can make a smooth sliding movement within the cylinder when driven by a coil, thereby reducing wear of the inner wall of the cylinder. As a result of inspection of the electromagnetic shut-off valve, it was confirmed that abrasion powder of Al was present in the cylinder. Although the amount of such powder was very small, it is assumed that the Al powder can be easily transferred into the graphite tube furnace when the gas flow rate is abruptly changed, for example, from 5 ml/min. to 200 ml/min. or vice versa.

Figure 6:
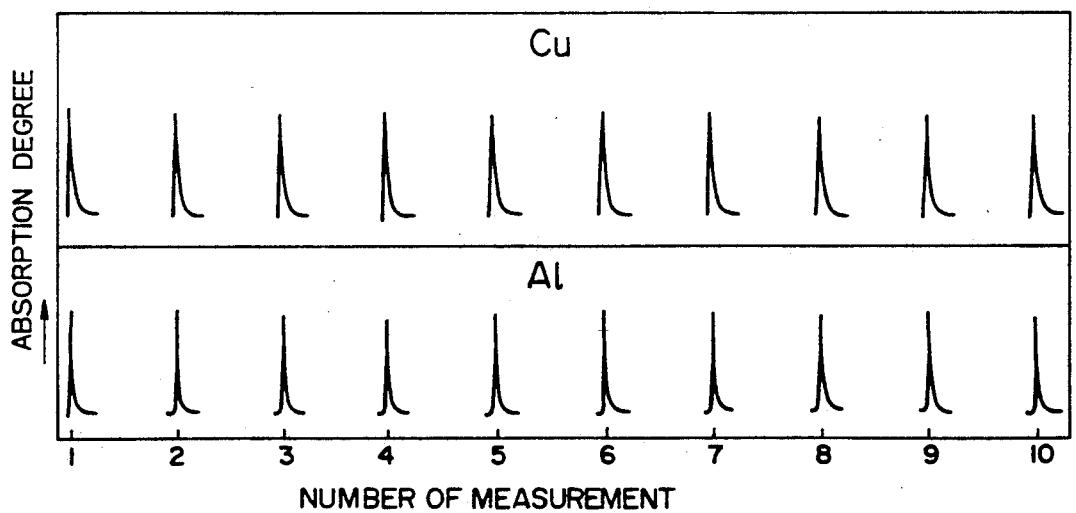
FIG. 6 is a diagrammatical illustration showing atomic absorption spectra of Al and Cu in a serum obtained using the spectrophotometer of the present invention.

FIG. 6 shows the results obtained when Al and Cu in a human serum were simultaneously subjected to an atomic absorption analysis under the conditions shown in Table 1, using the atomic absorption spectrophotometer of the present invention. The ordinate represents the absorption degree, and the abscissa represents the number of the measurement. As seen from FIG. 6, any extraordinarily high absorption signal was not recognized, and even one abnormal signal was not found at least in 100 measurements.

Figure 7:
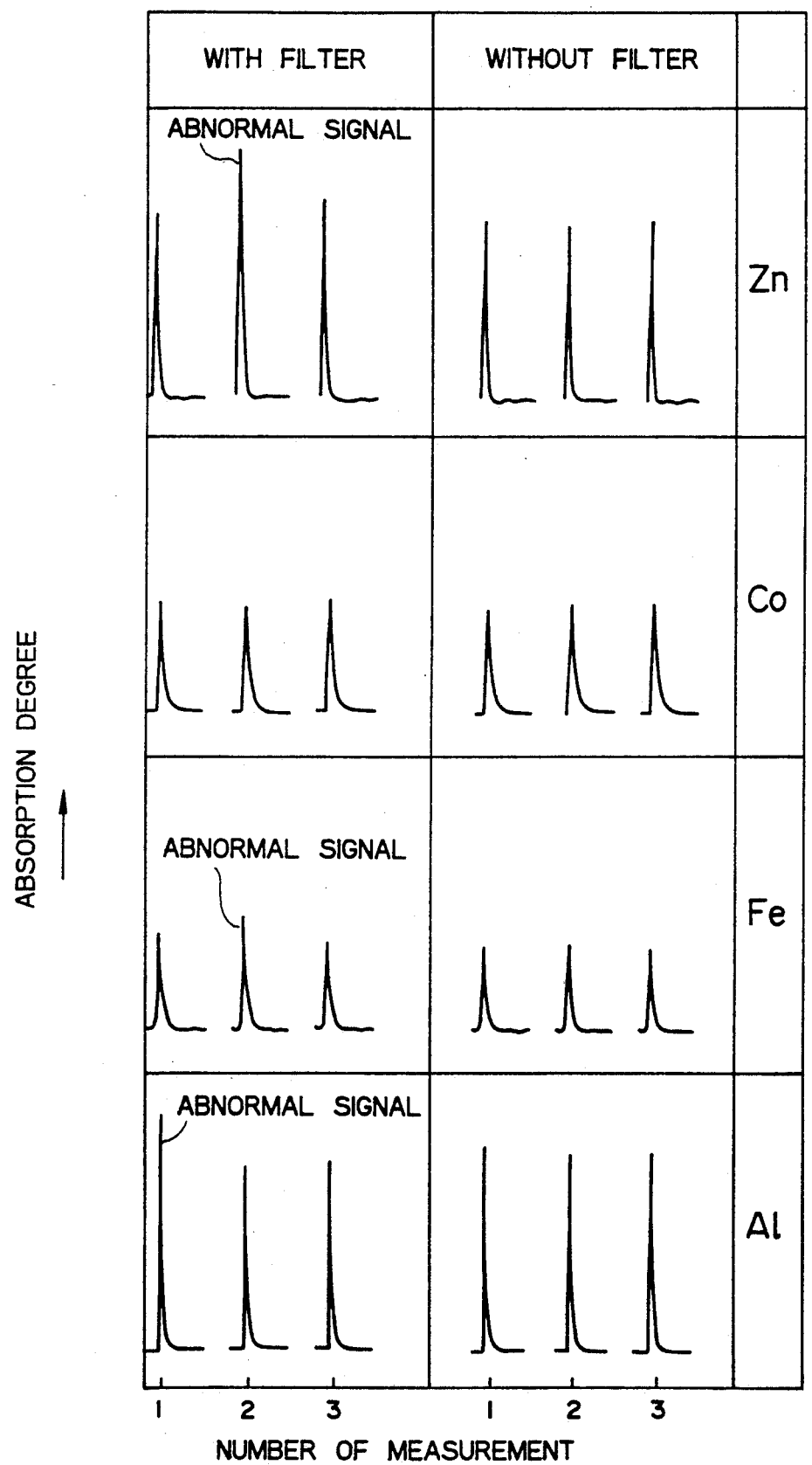
FIG. 7 is a diagrammatical illustration showing atomic absorption spectra of Al and Cu in a human serum obtained using a prior art spectrophotometer and the spectrophotometer of the present invention.

FIG. 7 shows atomic absorption spectra obtained when four elements of Al, Fe, Co and Zn contained in a standard sample were simultaneously subjected to an atomic absorption analysis under the conditions shown in Table 1, using the atomic absorption spectrophotometer of the present invention and a prior atomic absorption spectrophotometer not provided with the filter means. The ordinate represents the absorption degree, and the abscissa represents the number of the measurement. The amount of the sample was 0.02 ml. As seen from FIG. 7, in the prior atomic absorption spectrophotometer not provided with the filter means, abnormal peaks appeared with respect to Al, Fe, Zn, and these values were greater than their expected values, and besides they tend to be higher as compared with those obtained in the atomic absorption spectrophotometer of the present invention provided with the filter means. It is assumed that this is due to the fact that foreign matter containing those elements showing the above abnormal peaks were introduced into the graphite tube furnace in the prior atomic absorption spectrophotometer not provided with the filter means.

Although the present invention has been specifically described by way of the above preferred embodiment thereof, the invention itself is not to be restricted to such embodiment.

What is claimed is:

1. In an atomic absorption spectrophotometer wherein an amount of supply of an inert gas to a sample-atomizing portion is changed by the operation of a movable valve means according to an ashing step and an atomization step in the sample-atomizing portion, the improvement comprising filter means provided between said movable valve means and said sample-atomizing portion.

2. Spectrophotometer according to claim 1, in which said filter means comprises a filter element and a filter holder.

3. Spectrophotometer according to claim 2, in which said filter element is made of a polymeric organic film.

4. Spectrophotometer according to claim 2, in which said filter element is perforated, the diameter of the perforations being 0.05 to 0.50 μm.

5. Spectrophotometer according to claim 2, in which said filter holder is accessible so as to enable replacement of said filter element.

6. Spectrophotometer according to claim 1 or 2, in which said movable valve means is an electromagnetic shut-off valve, said sample-atomizing portion being constituted by a graphite tube furnace.

7. In an atomic absorption spectrophotometer comprising movable valve means for changing an amount of supply of an inert gas to a sample-atomizing portion according to an ashing step and an atomization step in said sample-atomizing portion, said sample-atomizing portion being provided downstream of and connected to said movable valve means, the improvement comprising first filter means provided immediately downstream of said movable valve means, and second filter means provided immediately upstream of said sample-atomizing portion.

8. Spectrophotometer according to claim 7, in which each of said first and second filter means comprises a filter element and a filter holder.

9. Spectrophotometer according to claim 8, in which said filter element is made of a polymeric organic film.

10. Spectrophotometer according to claim 8, in which said filter element is perforated, the diameter of the perforations being 0.05 to 0.50 μm.

11. Spectrophotometer according to claim 8, in which said filter holder is accessible so as to enable replacement of said filter element.

12. Spectrophotometer according to claim 7 or 8, in which said movable valve means is an electromagnetic shut-off valve, said sample-atomizing portion being constituted by a graphite tube furnace.

13. In an atomic absorption spectrophotometer comprising a sample-atomizing portion for ashing and atomizing a sample; a power source operable to supply electric current to said sample-atomizing portion; a controller for controlling the operation of said power source; a pair of pressure regulators for setting the flow rate of an inert gas according to an ashing step and an atomization step in said sample-atomizing portion; and a pair of movable valves respectively provided downstream of and connected to said pair of pressure regulators, either of said pair of movable valves being activated into an open or closed condition in synchronism with the operation of said power source so as to select the flow rate of the inert gas into said sample-atomizing portion; the improvement comprising filter means provided between said pair of movable valves and said sample-atomizing portion.

14. Spectrophotometer according to claim 13, in which said filter means comprises a filter element and a filter holder.

15. Spectrophotometer according to claim 14, in which said filter element is made of a polymeric organic film.

16. Spectrophotometer according to claim 14, in which said filter element is perforated, the diameter of the perforations being 0.05 to 0.50 μm.

17. Spectrophotometer according to claim 14, in which said filter holder is accessible so as to enable replacement of said filter element.

18. Spectrophotometer according to claim 13 or 14, in which each said movable valve is an electromagnetic shut-off valve, said sample-atomizing portion being constituted by a graphite tube furnace.

19. Spectrophotometer according to claim 1, in which said filter means comprises a filter element made of a polymeric organic film.

20. Spectrophotometer according to claim 7, in which each of said first and second filter means comprises a filter element made of a polymeric organic film.

21. Spectrophotometer according to claim 13, in which said filter means comprises a filter element made of a polymeric organic film.

* * * * *